United States Patent [19]

Powell et al.

[11] Patent Number: 5,961,967
[45] Date of Patent: Oct. 5, 1999

[54] MULTIPHASE CANDLE CONTAINING LOCALLY ENRICHED REGIONS OF DELIVERABLE ACTIVES

[75] Inventors: W. Nigel Powell, Stillwater; Daniel B. Pendergrass, Jr., Mendota Heights, both of Minn.

[73] Assignee: 3M Innovative Properties Company, St. Paul, Minn.

[21] Appl. No.: 08/708,281

[22] Filed: Sep. 6, 1996

[51] Int. Cl.$^6$ ............... A61L 9/02; A01N 25/20; C11C 5/00; A61K 9/10
[52] U.S. Cl. ............ 424/76.4; 424/484; 424/409; 424/501; 424/502; 425/803; 44/275
[58] Field of Search .................. 424/486, 484, 424/487, 497–98, 501–502, 409, 419, 420, 76.4, DIG. 8; 106/270; 425/803; 44/275; 427/212, 213.36, 443

[56] References Cited

U.S. PATENT DOCUMENTS

| | | | |
|---|---|---|---|
| 2,800,457 | 7/1957 | Green | 252/316 |
| 2,800,458 | 7/1957 | Green | 252/316 |
| 3,423,489 | 1/1969 | Arens | 264/4 |
| 3,505,432 | 4/1970 | Neuwald | 260/93.7 |
| 3,516,941 | 6/1970 | Matson | 252/316 |
| 3,565,819 | 2/1971 | Gragger | 424/498 |
| 3,689,616 | 9/1972 | Kelley . | |
| 3,745,213 | 7/1973 | Nysted | 424/19 |
| 3,779,942 | 12/1973 | Bolles | 252/316 |
| 3,797,990 | 3/1974 | Rogers et al. | 431/291 |
| 3,856,699 | 12/1974 | Miyano et al. | 424/498 |
| 4,230,687 | 10/1980 | Sair | 424/22 |
| 5,208,132 | 5/1993 | Kamada et al. . | |

FOREIGN PATENT DOCUMENTS 0 328 145  10/1989  European Pat. Off. .
2 199 246   7/1988  United Kingdom .

*Primary Examiner*—Edward J. Webman
*Attorney, Agent, or Firm*—Dale A. Bjorkman

[57] ABSTRACT

A candle is provided for delivery of an active ingredient comprising a multiphase construction of a continuous first matrix and a second matrix dispersed therein. The first matrix comprises a thermoplastic material, and the second matrix comprises a thermoplastic material which additionally comprises an active ingredient. The second matrix is a discrete phase of small bodies having size in longest dimension between about 0.05 microns to about 5 mm. The material of the second matrix is selected such that the Rate of Release of the second matrix containing the active ingredient is substantially the same as the Rate of Release of the first matrix and the Tested Physical Property of the multiphase construction is at least about 10% higher than the Tested Physical Property of a homogeneous combination of equivalent amounts of the first matrix material, the second matrix material and the active agent in at least one the tests selected from the group consisting of the Shear Strength Test, Active Migration Test, the Tensile Modulus Test or the Flexural Modulus Test.

32 Claims, No Drawings

MULTIPHASE CANDLE CONTAINING LOCALLY ENRICHED REGIONS OF DELIVERABLE ACTIVES

FIELD OF THE INVENTION

This invention relates to the delivery of active ingredients. More specifically, this invention relates to delivery of active ingredients from a multiphase article having an enriched phase dispersed in a continuous phase.

BACKGROUND OF THE INVENTION

Single phase delivery articles for active agents which release such agents by diffusion, by erosion or dissolution, or by combustion, for example, are well known. Examples include candles comprising fragrance components dissolved or dispersed in the wax and released by burning the candle and toilet bowl or urinal blocks which release fragrance, antimicrobials, colorants, and/or bleaches as the block is slowly dissolved. In this context, such articles will be considered single phase if the active agent is dispersed or dissolved uniformly throughout the bulk of the article. While minor inhomogeneities may be present in the continuous matrix of known articles, these inhomogeneities do not generally materially affect the active loading capacities of the articles.

In such articles, the mechanical properties of the finished article are frequently compromised by the presence of the active agent or agents within a single phase matrix, as defined herein. In the case where the active comprises an insoluble liquid dispersed uniformly throughout the solid matrix, the mechanical properties of the composite article may often be approximated by the volume weighted average of the properties of the matrix material and the corresponding properties of the liquid agent. This places a severe upper limitation on the total amount of liquid agents which may be incorporated without loss of rigidity in the finished article. In addition, the incorporation of large amounts of an incompatible agent may result in blooming or sweating of the agent at the surface of the article.

SUMMARY OF THE INVENTION

An article is provided for delivery of an active ingredient comprising a multiphase construction of a continuous first matrix and a second matrix dispersed therein. The first matrix comprises a thermoplastic material, and the second matrix comprises a thermoplastic material which additionally comprises an active ingredient. The second matrix is a discrete phase of small bodies having size in longest dimension between about 0.05 microns to about 5 mm. The material of the second matrix is selected such that the Rate of Release of the second matrix containing the active ingredient is substantially the same as the Rate of Release of the first matrix and the Tested Physical Property of the multiphase construction is at least about 10% higher than the Tested Physical Property of a homogeneous combination of equivalent amounts of the first matrix material, the second matrix material and the active agent in at least one the tests selected from the group consisting of the Shear Strength Test, Active Migration Test, the Tensile Modulus Test or the Flexural Modulus Test.

This multiphase article has significant advantages over articles of the prior art, wherein the amount of active material that could be included in a formulation is frequently severely limited by a reduction in the mechanical properties of the article which usually accompanies higher loadings. Considering these advantages from a commercial product viewpoint, the present invention provides articles that have superior delivery of active ingredient from an article having the same physical properties as commerically available articles, or may have superior physical properties to commercially available articles containing the same amount of active ingredient. As a specific example to these viewpoints, a fragranced candle may now be make having greater quantities of the active ingredient (fragrance) than was previously possible from a candle having the same tensile, modulus and active migration as prior art candles. On the other hand, citronella candles (having an insect repellant as an active ingredient) are notoriously soft as a commercial product. Using the present invention, citronella candles may now be manufactured having much improved physical properties, but with the same level of active ingredient in the candle available for delivery as in the currently available commercial product.

Also described are novel methods of making articles for delivery of active ingredients.

DETAILED DESCRIPTION OF THE INVENTION.

The present invention contemplates the manufacture and use of articles for delivery of active ingredients where the active is released to the environment by some mode of action involving a Rate of Release of active through a physical property of the matrix. The Rate of Release is defined as the rate at which the matrix is dissipated or releases active ingredient through the mode of release for that particular article. Typically, articles as contemplated release active ingredient through the mechanisms of abrasion, diffusion, melting or dissolution. Examples of articles and their primary mode of release include candles, which release active ingredients entrained within their matrix by melting, and urinal blocks, which release their active ingredient by dissolution. Toilet tank fragrance or cleaner dispensers may release active either through dissolution or diffusion. Crayons may release active ingredients (such as fragrance or any other active ingredient to be applied to a surface or to the surronding environment) through abrasion. Gel or solid air fresheners generally diffuse the active ingredient through the matrix. Solid stick topical application devices such as lip balm may dispense fragrance, flavorants or medicaments to the user either by abrasion or diffusion. Bath beads and aromatherapy agents are typically placed in hot or warm water and allowed to dissolve or melt. Other such delivery devices will now be apparent to the artisan.

Matrix materials are selected based on their physical properties at ambient temperature and under conditions of use. Both the first matrix and the second matrix materials may be selected from the same class of materials generally, except that the second matrix has physical properties that enable the final product to be manufactured without homogeneous mixing of the first matrix and the second matrix. Thus, the first and second matrix materials are selected such that they will maintain phase separation to provide discrete regions of the respective matrices. Typically the mode of mixing the matrices utilizes heating the first matrix to the melting point and mixing in the second fragrance-containing matrix. In this manufacturing technique, the melting point of the second fragrance-containing matrix must be higher than the effective manufacturing temperature of the final article.

Preferred matrix materials include various thermoplastic materials and mixtures thereof, such as natural or synthetic fatty alcohols, fatty acids, fatty esters and waxes or blends thereof Natural waxes include the vegetable waxes such as carnauba, cauassu, candelilla, raffia, palm, esparto, sugar cane and cotton waxes; animal waxes such as beeswax, ghedda, chinese insect, shellac, spermaceti and lanolin waxes; and mineral wax such as paraffin, microcrystalline, ozokerite, montan and syncera waxes. Synthetic and modified waxes useful as matrix materials include the Carbowaxes, Abril waxes, Armid and Armowaxes (Armour & Co.) and Chlorax chlorinated paraffin wax (Watford Chemical Co.). It will be appreciated that waxes are a mixture of various components, and that each type of wax is itself available in a number of different grades.

Other thermoplastic materials are useful as matrix materials, including polyethylenes such as Polywax™ from Petrolite, Inc., polypropylenes, polyesters, polyvinyl chlorides, tristarch acetates, polyethylene oxides, polypropylene oxides, polyvinylidene chloride or fluoride, polyvinyl alcohols, polyvinyl acetates, polyacrylates, polymethacrylates, vinyl functional polymers, urethanes, polycarbonates and polylactones or blends thereof.

Particularly preferred matrix materials carnuba wax, yellow beeswax, white beeswax, paraffin and linear or branched polyethylenes or blends thereof.

Most preferably, the matricies are selected such that they are solids at about 40° C.

As noted above, the second matrix comprises a thermoplastic material which additionally comprises one or more active ingredients. The second matrix is a discrete phase of small bodies of an average size in longest dimension between about 0.05 microns to about 5 mm. Preferred small bodies have an average size in longest dimension between about 4 and 200 microns. More preferably, the small bodies have an average size in longest dimension between about 40 and 150 microns, and most preferably, between about 80–120 microns. Larger discrete phases deliver much more volume of active ingredient per phase, and therefore are preferred for the present invention.

The second matrix may, for example, be essentially the same material as the first matrix, with the physical properties enhanced by incorporation of an additive that interacts physically or chemically with the material of the second matrix. An example of an additive to be incorporated into certain waxes in particular, for example carnauba wax, is polyethylene. While not being limited by theory, it is believed that such polymer additives act as a bridge or web to reinforce the particle as it cools. Preferably additives are provided to the matrix material in up to 5% of the matrix material.

The matrix material may optionally be provided with an additional filler component. Such a filler could reduce the cost of the matrix or modify the diffusion of the active component within the second matrix. For example, platelet shaped filler materials would provide additional resistance to escape of active component from the second matrix body by requiring the active component to travel a tortuous pathway in the diffusion process. Examples of filler materials include mica, barium ferrite, silica, graphite and powdered carbon.

It will be appreciated that the presence of small local concentrations of the active or actives as dispersed liquid droplets or solid crystals, or the intentionally introduced insoluble particulates such as fillers and colorants do not constitute a multiphase article for the purposes of this invention. The common utilization of colorant or fragrance concentrates by which the active agent or agents is introduced into the bulk material of the article as by melting the single continuous phase, together with the concentrate and any associated abherent coating, may result in such incidental inhomogeneities if mixing is incomplete. In so far as a primary, continuous matrix may be comprised of multiple components, for example, a blend of natural and synthetic waxes, some spontaneous phase separation may occur during solidification from a substantially homogeneous melt without producing a multiphase system in the sense of this invention even though one of the components of the continuous matrix may have a higher affinity for the active(s).

The melting temperature or the melt flow temperature of the combined second matrix material and the associated actives is preferably at least 10° C. above the corresponding melting temperature or the melt flow temperature of the first matrix material and preferably should be at least 20° C. above said temperature to allow incorporation of the second matrix material as a solid within the molten first matrix material during processing without undue mixing of the phases. If said melt temperature is greater than about 35° C., it is likely that at least a portion of the potential capacity of the particle is not being used efficiently. If the second phase is enclosed in a substantially continuous coating, it may melt below the melting point of the of the first matrix providing that the coating remains intact during the fabrication processes. In the absence of a continuous coating, it is preferable to coat the surface of the second matrix phase with a particulate which serves as a mechanical barrier to the migration of the active(s) and reduces the apparent area of the interface between the phases through which the active(s) may migrate. Such particulates may also serve as an abherent to limit premature fusion of individual particles of the second phase prior to their incorporation into the first matrix. A less preferred embodiment would replace the surface coating on the second matrix particle with internal particulate barriers to diffusion of the active(s) within the second matrix phase. While such internal particles may be combined with the preferred coating, they will usually simply replace potentially active material with a relatively inefficient barrier and will contribute to the amount of undesirable debris in the article that will interfere with release of the active material. In the discussion, the assumption has been made that the second phase will be provided as small spheres to minimize the amount of coating material in the final item, however it is apparent that rods, cubes, or other shapes may be employed if decorative effects are desired.

The material of the second matrix is selected such that the Rate of Release of the second matrix containing the active ingredient is substantially the same as the Rate of Release of the first matrix. For example, a candle of the present invention will burn evenly without collection of one matrix in the melt pool of the candle. Likewise, a urinal block of the present invention will not preferentially dissolve one matrix before the other to leave particulate matrix residue. An evaluation of Rate of Release is therefor properly taken under conditions of use to determine whether the selection of matrix materials is properly matched for the article to be fabricated.

The matrix of the second phase is selected such that it remains separate and intact during the fabrication of the completed article and such that the matrix, loaded with the desired level of active agent or agents, maintains mechanical properties similar to those of the unmodified, continuous matrix which forms the article. The integrity of the second, active containing phase may optionally be maintained or enhanced by the presence of a coating that is continuous discontinuous, and that is resinous in nature or formed by an agglomeration of discrete particles at the interface between the two phases. If such a coating is present, it should not significantly interfere with the release of the active as the article is consumed. Examples of such coatings include chicle-type resins or solid filler particles or flakes that will agglomerate at the interface of the two matrices, thereby creating a physical barrier to slow the migration of the active ingredient from the second matrix body.

As noted above, the Tested Physical Property of the multiphase construction is at least about 10% higher than the Tested Physical Property of a homogeneous combination of equivalent amounts of the first matrix material, the second matrix material and the active agent in at least one the tests selected from the group consisting of the Shear Strength Test, Active Migration Test, the Tensile Modulus Test or the Flexural Modulus Test. Thus, the article of the present invention is capable of delivering more or the same amount of active ingredient from a system having superior storage, transportability and use properties.

The Shear Strength Test is carried out according to ASTM test D 732-90. This test is carried out over the entire range of temperature to which an article would be exposed in commercial storage and shipping. If a 10% difference in properties is observed at any single temperature in this range, the article is deemed to pass this test. Most articles being shipped in conventional commerce routes, i.e. truck, train and the like that are not provided with climate control may be expected to be exposed to temperatures between −40° C. and 50° C.

The Active Migration Test is carried out in a manner similar to ASTM test C 772-90, with the following parameters. A 4 cm×4 cm×1.25 cm sample is placed on its large face on 3 filter papers (high grade, rapid) that are 7.62 cm in diameter, and allowed to reside there for one week at the test temperature. The filter paper is examined by viewing from the back side when held up to light. The sample is deemed to pass this test (exhibit the desired level of improvement in physical properties) if there is no stain on the second sheet of filter paper.

The Flexural Modulus Test is carried out according to ASTM test D 5023-89, with the frequency of dynamic linear displacement being 100 Hz and the linear displacement amplitude being 2% of the sample width. This test is carried out over the entire range of temperature to which an article would be exposed in commercial storage and shipping. If a 10% difference in properties is observed at any single temperature in this range, the article is deemed to pass this test. Most articles being shipped in conventional commerce routes, i.e. truck, train and the like that are not provided with climate control may be expected to be exposed to temperatures between −40 C and 50 C.

The Tensile Modulus Test is carried out according to ASTM test D 5026-89, with the frequency of dynamic linear displacement being 100 Hz and the linear displacement amplitude being 2% of the sample width. This test is carried out over the entire range of temperature to which an article would be exposed in commercial storage and shipping. If a 10% difference in properties is observed at any single temperature in this range, the article is deemed to pass this test. Most articles being shipped in conventional commerce routes, i.e. truck, train and the like that are not provided with climate control may be expected to be exposed to temperatures between −40° C. and 50° C.

The second matrix may be incorporated within the first matrix in the form of bodies having various shapes, such as spherical, ovoid, rectangular or prismatic, stripes, cores within shells, ribbons, and the like. Different colors, pigments or reflective materials may be incorporated in one or more of the phases to achieve optionally visual disinctness of discrete particles, thereby distinguishing the article for aesthetic or identification purposes.

As an alternative, the second matrix may be provided as coating over a fragrance-loaded particle. The coating must be selected to survive the molding process for the first matrix. The inside of the coated particle can have the same or even a lower melting point than the first matrix. Optionally, the inner material of the coated particle may be a liquid fill.

When the second matrix is a coating over a particle or liquid, the materials may be manufactured using techniques known in the encapsulation art, such as bitubular injection capsules as disclosed in U.S. Pat. No. 3,423,489, to Arens, et.al and U.S. Pat. No. 3,779,942, to Bolles. Another type of manufacure technique useful in the present invention is described in U.S. patent application Ser. No 08/123,806, filed Sep. 20, 1993, the disclosure of which is incorporated herein by reference.

A wax candle containing harder, higher melting wax particles highly loaded with fragrance oil and coated with an occlusive particulate will serve as an illustrative example of the multiphase articles of this invention. The candle may be fabricated, by conventional melt casting or dipping, from an appropriate first matrix material, such as ordinary candle wax, in which are dispersed particles of an initially higher melting point second matrix material, such as another wax, containing the active agent or agents. The second matrix material is selected to provide mechanical properties similar to those of the first matrix material even when highly loaded with the actives and further selected to maintain a melting or flow point above the minimum melt processing temperature of the first matrix such that it remains as discrete particles within the first matrix during candle formation. This sequestration of phases may be enhanced by the presence of a coating or a layer of abherent materials at the surface of the discrete particles. This stabilizing layer may optionally contribute color to the overall item as well as providing an optional occlusive barrier to the migration of the active from the enriched phase into the conventional continuous phase. Even if components of the stabilizing layer, if any, were the same as the adsorptive fillers of the prior art, they could be present in much lower total concentration since they are required only at the surface of the active enriched phase.

Articles according to the present invention may be manufactured according to techniques generally known in the art, except that in the present invention first the active ingredient is incorporated into the second matrix, and the second matrix is then mixed with the first matrix to form the final article such that discrete bodies of the second matrix are dispersed within the first matrix.

The articles made according to the present invention have significant advantages as compared to prior art articles, such as candles and urinal blocks. More actives, such as fragrance, can be delivered from the inventive articles. The articles so made are easier to manufacture because they have good physical integrity. The articles are more readily removed from molds and do not sag in moderately warm temperatures. Preferably, the present articles exhibit good durometer hardness at 90 degree F temperature.

Active ingredients that may be delivered from articles according to the present invention are any appropriate for delivery in either a slow release or on-demand release format. Examples of such actives include fragrances, insect repellants, medicaments, aromatherapy agents, and the like. While the predominant amount of active ingredient is to be located in the second matrix, it is contemplated that insubstantial amounts of active ingredient may be provided in the first matrix. That is, the amount of active ingredient residing in the first matrix will not be sufficient to significantly deleteriously effect the Tested Physical Properties of the first matrix.

The following examples are provided for purposes of illlustrating the invention, and are not to be construed to limit the scope of the presently contemplated invention.

EXAMPLE 1

A fragrance rich particle was produced by adding one part by weight of a Vanilla fragrance oil, available from Intercontinental Fragrance as FG0471 to one part molten Polyset® 2015 [a hard, high melting point polyethylene wax from IGI International Waxes, Agincourt, Ontario, Canada, drop melting point 115° C. (ASTM D127)], cooling to solidify, and then cryogrinding to produce a particulate. One part of the particulate was then added to 4 parts of a candle wax blend (Candle Magic, Cornflower Blue # 51210, obtained from Distlefink Designs, Inc., South Britain, Conn.) which had been premelted (54° C.) in a double boiler. The resulting mixture was then cast in a candle mold with a wick (Candle Magic, Center Burning—Wax Coated # 51601, obtained from Distlefink Designs, Inc., South Britain, Conn.). The resulting candle burns with a fragrant flame. Microscopic examination of a thin section of the candle indicates that the fragrance rich particles have been maintained as a discrete phase.

EXAMPLE 2

A fragrance rich particle was produced by adding one part by weight of a Forest fragrance oil, available from Intercontinental Fragrance as FG8077 to one part molten Polyset® 2015 [IGI International Waxes, Agincourt, Ontario, Canada, drop melting point 115° C. (ASTM D127)], cooling to solidify, and then cryogrinding to produce a particulate. One part of the particulate was then added to 4 parts of a candle wax blend (Candle Magic, Cornflower Blue # 51210, obtained from Distlefink Designs, Inc., South Britain, Conn.) which had been premelted (54° C.) in a double boiler. The resulting mixture was then cast in a candle mold with a wick (Candle Magic, Center Burning—Wax Coated # 51601, obtained from Distlefink Designs, Inc., South Britain, Conn.). The resulting candle burns with a fragrant flame. Microscopic examination of a thin section of the candle indicates that the fragrance rich particles have been maintained as a discrete phase.

What is claimed:

1. A candle for delivery of an active ingredient comprising a construction of a continuous first matrix and a second matrix dispersed therein, wherein the first matrix comprises a thermoplastic material, and the second matrix comprises a thermoplastic material which additionally comprises an active ingredient; wherein said second matrix is a discrete phase of small bodies having size in longest dimension between about 0.05 microns to about 5 mm, and the material of said second matrix is selected such that the Rate of Release of the second matrix containing the active ingredient is the same as the Rate of Release of the first matrix and the construction passes the Shear Strength Test.

2. The candle of claim 1 wherein the first and second matrices are solid at about 40° C.

3. The candle of claim 1 wherein the active ingredient comprises a fragrance.

4. The candle of claim 1 wherein the active ingredient comprises an insect repellant.

5. The candle of claim 1 wherein the active ingredient comprises citronella.

6. The candle of claim 1 wherein the active ingredient comprises a medicament.

7. The candle of claim 1 wherein the active ingredient comprises an anti-microbial.

8. The candle of claim 1 wherein the active ingredient comprises an aromatherapy agent.

9. A candle for delivery of an active ingredient comprising a construction of a continuous first matrix and a second matrix dispersed therein, wherein the first matrix comprises a thermoplastic material, and the second matrix comprises a thermoplastic material which additionally comprises an active ingredient; wherein said second matrix is a discrete phase of small bodies having size in longest dimension between about 0.05 microns to about 5 mm, and the material of said second matrix is selected such that the Rate of Release of the second matrix containing the active ingredient is the same as the Rate of Release of the first matrix and the construction passes the Active Migration Test.

10. The candle of claim 9 wherein the first and second matrices are solid at about 40° C.

11. The candle of claim 9 wherein the active ingredient comprises a fragrance.

12. The candle of claim 9 wherein the active ingredient comprises an insect repellant.

13. The candle of claim 9 wherein the active ingredient comprises citronella.

14. The candle of claim 9 wherein the active ingredient comprises a medicament.

15. The candle of claim 9 wherein the active ingredient comprises an anti-microbial.

16. The candle of claim 9 wherein the active ingredient comprises an aromatherapy agent.

17. A candle for delivery of an active ingredient comprising a construction of a continuous first matrix and a second matrix dispersed therein, wherein the first matrix comprises a thermoplastic material , and the second matrix comprises a thermoplastic material which additionally comprises an active ingredient; wherein said second matrix is a discrete phase of small bodies having size in longest dimension between about 0.05 microns to about 5 mm, and the material of said second matrix is selected such that the Rate of Release of the second matrix containing the active ingredient is the same as the Rate of Release of the first matrix and the construction passes the Flexural Modulus Test.

18. The candle of claim 17 wherein the first and second matrices are solid at about 40° C.

19. The candle of claim 17 wherein the active ingredient comprises a fragrance.

20. The candle of claim 17 wherein the active ingredient comprises an insect repellant.

21. The candle of claim 17 wherein the active ingredient comprises citronella.

22. The candle of claim 17 wherein the active ingredient comprises a medicament.

23. The candle of claim 17 wherein the active ingredient comprises an anti-microbial.

24. The candle of claim 17 wherein the active ingredient comprises an aromatherapy agent.

25. A candle for delivery of an active ingredient comprising a construction of a continuous first matrix and a second matrix dispersed therein, wherein the first matrix comprises a thermoplastic material, and the second matrix comprises a thermoplastic material which additionally comprises an active ingredient; wherein said second matrix is a discrete phase of small bodies having size in longest dimension between about 0.05 microns to about 5 mm, and the material of said second matrix is selected such that the Rate of Release of the second matrix containing the active ingredient is the same as the Rate of Release of the first matrix and the construction passes the Tensile Modulus Test.

26. The candle of claim 25 wherein the first and second matrices are solid at about 40° C.

27. The candle of claim 25 wherein the active ingredient comprises a fragrance.

28. The candle of claim 25 wherein the active ingredient comprises an insect repellant.

29. The candle of claim 25 wherein the active ingredient comprises citronella.

30. The candle of claim 25 wherein the active ingredient comprises a medicament.

31. The candle of claim 25 wherein the active ingredient comprises an anti-microbial.

32. The candle of claim 25 wherein the active ingredient comprises an aromatherapy agent.

* * * * *